United States Patent
Taylor et al.

(10) Patent No.: US 12,059,288 B2
(45) Date of Patent: *Aug. 13, 2024

(54) SYSTEMS AND METHODS FOR ASSESSING THE SEVERITY OF PLAQUE AND/OR STENOTIC LESIONS USING CONTRAST DISTRIBUTION PREDICTIONS AND MEASUREMENTS

(71) Applicant: HeartFlow, Inc., Redwood City, CA (US)

(72) Inventors: Charles A. Taylor, Atherton, CA (US); Leo Grady, Darien, CT (US); Sethuraman Sankaran, Palo Alto, CA (US); Souma Sengupta, Cupertino, CA (US); Hyun Jin Kim, San Mateo, CA (US); Nan Xiao, San Jose, CA (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,076

(22) Filed: May 12, 2022

(65) Prior Publication Data

US 2022/0265239 A1 Aug. 25, 2022

Related U.S. Application Data

(63) Continuation of application No. 16/396,356, filed on Apr. 26, 2019, now Pat. No. 11,357,469, which is a
(Continued)

(51) Int. Cl.
*A61B 6/00* (2024.01)
*A61B 5/026* (2006.01)
(Continued)

(52) U.S. Cl.
CPC .............. *A61B 6/563* (2013.01); *A61B 5/026* (2013.01); *A61B 6/032* (2013.01); *A61B 6/504* (2013.01);
(Continued)

(58) Field of Classification Search
CPC ......... A61B 5/026; A61B 6/032; A61B 6/504; A61B 6/507; A61B 6/5217; A61B 6/563;
(Continued)

(56) References Cited

U.S. PATENT DOCUMENTS 8,157,742 B2   4/2012   Taylor
8,311,748 B2   11/2012  Taylor et al.
(Continued)

FOREIGN PATENT DOCUMENTS

JP   2009518097 A   5/2009
WO   2006020792 A2  2/2006
WO   2014134289 A1  9/2014

OTHER PUBLICATIONS

International Search Report and the Written Opinion issued in related PCT/US16/042325 dated Sep. 23, 2016 (6 pages).

*Primary Examiner* — Michael T Rozanski
(74) *Attorney, Agent, or Firm* — Bookoff McAndrews, PLLC

(57) ABSTRACT

Systems and methods are disclosed for assessing the severity of plaque and/or stenotic lesions using contrast distribution predictions and measurements. One method includes: receiving patient-specific images of a patient's vasculature and a measured distribution of a contrast agent delivered through the patient's vasculature; associating the measured distribution of the contrast agent with a patient-specific anatomic model of the patient's vasculature; defining physiological and boundary conditions of a blood flow model of the patient's blood flow and pressure; simulating the distri-
(Continued)

bution of the contrast agent through the patient-specific anatomic model; comparing the measured distribution of the contrast agent and the simulated distribution of the contrast agent through the patient-specific anatomic model to determine whether a similarity condition is satisfied; and updating the defined physiological and boundary conditions and re-simulating distribution of the contrast agent through the one or more points of the patient-specific anatomic model until the similarity condition is satisfied.

20 Claims, 8 Drawing Sheets

Related U.S. Application Data continuation of application No. 15/210,712, filed on Jul. 14, 2016, now Pat. No. 10,307,131.

(60) Provisional application No. 62/193,994, filed on Jul. 17, 2015.

(51) Int. Cl.
*A61B 6/03* (2006.01)
*A61B 6/50* (2024.01)
*A61B 8/06* (2006.01)
*A61B 8/08* (2006.01)
*G06T 7/00* (2017.01)
*G16H 50/50* (2018.01)

(52) U.S. Cl.
CPC ............ *A61B 6/507* (2013.01); *A61B 6/5217* (2013.01); *A61B 8/06* (2013.01); *A61B 8/481* (2013.01); *G06T 7/0012* (2013.01); *G16H 50/50* (2018.01); *G06T 2207/10081* (2013.01); *G06T 2207/30101* (2013.01); *G06T 2207/30104* (2013.01)

(58) Field of Classification Search
CPC . A61B 8/06; A61B 8/481; G06T 2207/10081; G06T 2207/30101; G06T 2207/30104; G06T 7/0012; G16H 50/50
See application file for complete search history.

(56) References Cited

U.S. PATENT DOCUMENTS

| | | |
|---|---|---|
| 8,315,812 B2 | 11/2012 | Taylor |
| 8,315,814 B2 | 11/2012 | Taylor et al. |
| 8,386,188 B2 | 2/2013 | Taylor et al. |
| 8,594,950 B2 | 11/2013 | Taylor |
| 8,734,357 B2 | 5/2014 | Taylor |
| 9,070,214 B1 | 6/2015 | Grady et al. |
| 10,307,131 B2 | 6/2019 | Taylor et al. |
| 11,357,469 B2 * | 6/2022 | Taylor ................... G16H 50/50 |
| 2012/0041301 A1 | 2/2012 | Redel |
| 2014/0058715 A1 | 2/2014 | Sharma et al. |
| 2014/0243662 A1 | 8/2014 | Mittal et al. |
| 2015/0038860 A1 | 2/2015 | Fonte et al. |

* cited by examiner

SYSTEMS AND METHODS FOR ASSESSING THE SEVERITY OF PLAQUE AND/OR STENOTIC LESIONS USING CONTRAST DISTRIBUTION PREDICTIONS AND MEASUREMENTS

CROSS-REFERENCE TO RELATED APPLICATION(S)

This application is a continuation of and claims the benefit of priority to U.S. application Ser. No. 16/396,536, filed Apr. 26, 2019, which is a continuation of and claims the benefit of priority to U.S. patent application Ser. No. 15/210,712, filed Jul. 14, 2016, now U.S. Pat. No. 10,307,131, which claims priority to U.S. Provisional Application No. 62/193,994, filed Jul. 17, 2015, the entireties of which are hereby incorporated herein by reference.

FIELD OF THE DISCLOSURE

Various embodiments of the present disclosure relate generally to non-invasive cardiovascular disease assessment, treatment planning, and related methods. More specifically, particular embodiments of the present disclosure relate to systems and methods for non-invasively assessing blood flow characteristics using measurements and estimates of contrast distribution.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

Heart disease is typically viewed as resulting from vessel disease, in particular, narrowing or blockage inside vessel lumens in a way that impacts blood flow. Patient-specific modeling of blood flow in the circulation may include three or more elements: first, a description of the anatomic region of interest; second, the mathematical "governing equations" enumerating the physical laws of blood flow within the region of interest; and, third, "boundary conditions" to define physiologic relationships between variables at the boundaries of the region of interest. While the anatomic region of interest and the boundary conditions may be unique to each patient and the specific vascular territory, the governing equations describing velocity and pressure may be universal and apply in different patients and other arterial beds.

Three-dimensional models of blood flow may employ numerical methods to solve the Navier-Stokes equations governing fluid dynamics. In the last 25 years, three-dimensional numerical methods have become a standard approach for simulating blood flow in arteries. One technique includes simulating blood flow in patient-specific models derived from medical imaging data, combining three-dimensional models of blood flow in the large arteries with one-dimensional and lumped parameter models of arteries upstream or downstream of the regions of interest, and solving the coupled problems of blood flow and vessel wall dynamics. This coupling between three-dimensional models and reduced order models enable the solution of realistic coronary artery flow and pressure waveforms.

The ability to quantify blood flow in the human coronary arteries using image-based, patient-specific modeling has enabled the noninvasive quantification of fractional flow reserve (FFR). FFR may be defined by the ratio of maximal hyperemic flow to part of the myocardium in the presence of coronary artery disease to the maximum hyperemic flow to the same myocardial territory in the hypothetical case where the supplying vessels are normal. Clinically, FFR is measured invasively using a pressure-wire inserted into the coronary artery during cardiac catheterization by the ratio of distal perfusion pressure to aortic pressure under conditions of pharmacologically-induced maximum hyperemia. FFR can uniquely identify epicardial obstructive disease that is limiting hyperemic flow and may be correctable by percutaneous coronary intervention (PCI). A recommended threshold separating a positive from a negative FFR may be a predetermined value of 0.80, i.e. when the distal coronary pressure is 80% of the aortic pressure under conditions of maximal hyperemia. Deferral of PCI for vessels with an FFR>0.80 may improve clinical outcomes and reduce costs compared to angiography guided intervention. PCI in vessels with a measured FFR≤0.80 may reduce the combined end-point of death, myocardial infarction, and urgent revascularization as compared to optimal medical therapy. Current guidelines on myocardial revascularization assign a class I-A recommendation to FFR for the assessment of coronary artery stenoses with a diameter reduction ranging from 50 to 90% unless there is non-invasive proof of ischemia. There is a strong motivation to obtain FFR data noninvasively to determine which patients to refer to, or defer from, cardiac catheterization. Since FFR cannot be directly measured noninvasively, it is necessary to identify a surrogate that can be determined and which correlates with invasive FFR.

While evidence for the clinical benefit of fractional flow reserve is substantial, invasive determination of FFR can be expensive and not free of complications. Hence, there is a strong motivation to obtain this data noninvasively to determine which patients to refer to, or defer from, cardiac catheterization. Due to difficulties in noninvasive measurement of coronary artery blood pressure and flow, and in direct measurement of FFR, it has become advantageous to identify a surrogate that can be determined and which correlates with invasive FFR.

One method to noninvasively determine FFR is the simulation of coronary hemodynamics using computational fluid dynamics based on coronary artery anatomy as determined by FFR computed tomography (FFRCT). FFRCT has emerged as a viable alternative to anatomic or physiologic surrogates for invasively-measured FFR. FFRCT technology uses computational fluid dynamics to quantify the ratio of coronary artery to aortic pressure under conditions of simulated maximal hyperemia in a patient-specific anatomic and physiologic model derived from coronary CT angiography data and established biologic principles relating form (anatomy) to function (physiology). The diagnostic performance of FFRCT has been evaluated in three prospective, multicenter clinical trials in over 600 patients and more than 1000 vessels using FFR as the reference standard. In each study, FFRCT showed good correlation to FFR and demonstrated significant improvement in diagnostic accuracy and specificity, without sacrificing sensitivity, compared to anatomic assessment by coronary CT angiography alone.

However, the current correlation between FFRCT and measured FFR has room for improvement. One potential means to improve this technology would be to improve the estimation of coronary boundary conditions which define physiologic relationships between variables at the boundaries of the region of interest. These boundary conditions may encode flow, pressure, or a relationship between pressure and flow, such as impedance or resistance. In some implementations, the boundary conditions may be derived using form-function relationships from the CT anatomic data. A means to estimate these boundary conditions using other data available in the images would be highly advantageous. One potential approach that has been proposed to derive flow data from CT images is Transluminal Attenuation Flow Encoding (TAFE) where flow rate is inferred from gradients of contrast intensity along the length of the vessel and information about the time-dependent changes in the arterial contrast. A shortcoming of the TAFE approach is that it relies on a significant idealization of the coronary artery geometry and simplistic transport models. For example, the TAFE method involves the assumption that the ratio of flow to area does not change significantly along the length of the vessel, which would be violated in coronary artery stenoses where flow is constant but area changes significantly. Thus, while this approach has demonstrated promise in animal models, its utility in computing blood flow in patients is unproven. Performance has also been demonstrated only on single isolated lesions, and with either serial lesions or models with competing lesions in two branching vessels, the boundary condition approximation is/may not be valid. Further, the assumption of maximum dispersion occurring at outlets can be inaccurate depending on imaging resolution relative to outlet size and extent of disease burden. Thus, there is a desire for a system for quantification of blood that improves the estimation of coronary boundary conditions which define physiologic relationships between variables at the boundaries of the region of interest.

SUMMARY

The foregoing general description and the following detailed description are exemplary and explanatory only and are not restrictive of the disclosure. According to certain aspects of the present disclosure, systems and methods are disclosed for assessing the severity of plaque and/or stenotic lesions using contrast distribution predictions and measurements.

One method includes: receiving one or more patient-specific images of at least a portion of a patient's vasculature and a measured distribution of a contrast agent delivered through the patient's vasculature; associating the measured distribution of the contrast agent at points of the patient's vasculature with one or more points of a patient-specific anatomic model of the patient's vasculature generated using the received patient-specific images; defining one or more physiological and boundary conditions of a blood flow model for non-invasively estimating the patient's blood flow and pressure and simulating a distribution of the contrast agent through the patient-specific anatomic model of the patient's vasculature; simulating, using a processor, the distribution of the contrast agent through one or more points of the patient-specific anatomic model using the defined one or more physiological and boundary conditions; comparing, using a processor, the measured distribution of the contrast agent and the simulated distribution of the contrast agent through the patient-specific anatomic model to determine whether a similarity condition is satisfied; updating the defined physiological and boundary conditions and re-simulating the distribution of the contrast agent through the one or more points of the patient-specific anatomic model until the similarity condition is satisfied; calculating, using a processor, one or more blood flow characteristics of blood flow through the patient-specific anatomic model based on the updated physiological and boundary conditions; and outputting one or more of: the simulated contrast distribution, the one or more calculated blood flow characteristics, and the patient-specific anatomic model to an electronic storage medium or display.

In accordance with another embodiment, a system for assessing the severity of plaque and/or stenotic lesions using contrast distribution predictions and measurements comprises: a data storage device storing instructions for assessing the severity of plaque and/or stenotic lesions using contrast distribution predictions and measurements; and a processor configured for: receiving one or more patient-specific images of at least a portion of a patient's vasculature and a measured distribution of a contrast agent delivered through the patient's vasculature; associating the measured distribution of the contrast agent at points of the patient's vasculature with one or more points of a patient-specific anatomic model of the patient's vasculature generated using the received patient-specific images; defining one or more physiological and boundary conditions of a blood flow model for non-invasively estimating the patient's blood flow and pressure and simulating a distribution of the contrast agent through the patient-specific anatomic model of the patient's vasculature; simulating, using a processor, the distribution of the contrast agent through one or more points of the patient-specific anatomic model using the defined one or more physiological and boundary conditions; comparing, using a processor, the measured distribution of the contrast agent and the simulated distribution of the contrast agent through the patient-specific anatomic model to determine whether a similarity condition is satisfied; updating the defined physiological and boundary conditions and re-simulating the distribution of the contrast agent through the one or more points of the patient-specific anatomic model until the similarity condition is satisfied; calculating, using a processor, one or more blood flow characteristics of blood flow through the patient-specific anatomic model based on the updated physiological and boundary conditions; and outputting one or more of: the simulated contrast distribution, the one or more calculated blood flow characteristics, and the patient-specific anatomic model to an electronic storage medium or display.

In accordance with another embodiment, a non-transitory computer readable medium for use on a computer system containing computer-executable programming instructions for performing a method of assessing the severity of plaque and/or stenotic lesions using contrast distribution predictions and measurements, the method comprising: receiving one or more patient-specific images of at least a portion of a patient's vasculature and a measured distribution of a contrast agent delivered through the patient's vasculature; associating the measured distribution of the contrast agent at points of the patient's vasculature with one or more points of a patient-specific anatomic model of the patient's vasculature generated using the received patient-specific images; defining one or more physiological and boundary conditions of a blood flow model for non-invasively estimating the patient's blood flow and pressure and simulating a distribution of the contrast agent through the patient-specific anatomic model of the patient's vasculature, simulating, using a processor, the distribution of the contrast agent through one or more points of the patient-specific anatomic model using the defined one or more physiological and boundary conditions; comparing, using a processor, the measured distribution of the contrast agent and the simulated distribution of the contrast agent through the patient-specific anatomic model to determine whether a similarity condition is satisfied; updating the defined physiological and boundary conditions and re-simulating the distribution of the contrast agent through the one or more points of the patient-specific anatomic model until the similarity condition is satisfied; calculating, using a processor, one or more blood flow characteristics of blood flow through the patient-specific anatomic model based on the updated physiological and boundary conditions, and outputting one or more of: the simulated contrast distribution, the one or more calculated blood flow characteristics, and the patient-specific anatomic model to an electronic storage medium or display.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 5 may include an exemplary method of performing steps 412 of method 400 in FIG. 4.

FIG. 6 may include an exemplary method of performing step 216 of method 200 in FIG. 2.

FIG. 7 may include an exemplary method of performing step 218 of method 200 in FIG. 2.

FIG. 8 may include an exemplary method of performing step 220 of method 200 in FIG. 2.

DESCRIPTION OF THE EMBODIMENTS

Figure 1:
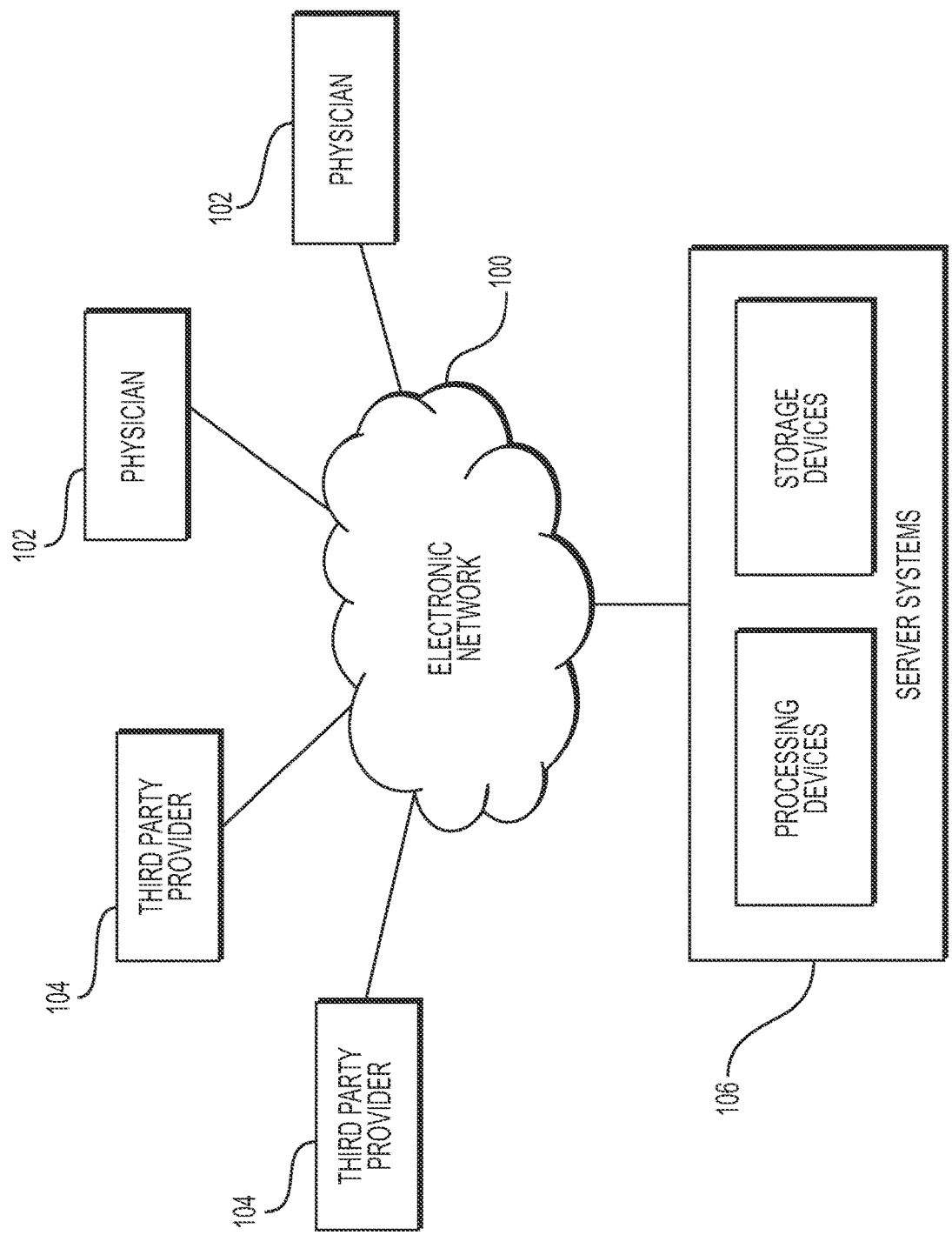
FIG. 1 is a block diagram of an exemplary system and network for assessing the severity of plaque and/or stenotic lesions using contrast distribution predictions and measurements, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

As described above, a desire exists for systems and methods for quantifying blood flow characteristics using improved estimation of coronary boundary conditions that define physiologic relationships between variables at the boundaries of the region of interest. Accordingly, the present disclosure describes systems and methods for improving the current correlation between FFRCT and measured FFR by making the estimation of coronary boundary conditions which define physiologic relationships between variables at the boundaries of the region of interest more accurate. These boundary conditions may encode flow, pressure, or a relationship between pressure and flow, such as impedance or resistance. In some implementations, the boundary conditions may be derived using form-function relationships from the CT anatomic data. The present disclosure also provides systems and methods for estimating these boundary conditions using other data available in the images. While blood flow characteristics may be inferred from gradients of contrast intensity along the vascular network, the systems and methods of the present disclosure overcomes the shortcomings of the Transluminal Attenuation Flow Encoding (TAFE) approach. For example, the systems and methods of the present disclosure may allow the possibility where the ratio of flow to area may change significantly along the length of the vessel as in, for example, coronary artery stenoses, where flow is constant but area changes significantly. Furthermore, the present disclosure may demonstrate utility in computing blood flow in patients, may demonstrate performance not only on single isolated lesions, but also serial lesions and/or models with competing lesions in two branching vessels.

The systems and methods of the present disclosure result in significant improvements in the quantification of blood flow from patient-specific medical imaging data. An overview of this approach is as follows. Blood flow may be computed, along with pressure and contrast distribution. The predicted to measured contrast distribution may be compared, and information may be used about the differences between predicted and measured contrast distribution to improve the original flow computation with the expectation that it would more closely match the unknown actual blood flow and pressure in the patient. A three-dimensional patient-specific anatomic model may be extracted from medical imaging data. A first set of boundary conditions may be defined, for example, using form-function relationships between the extracted coronary artery anatomy and a population-based physiology model. Blood flow velocity and pressure fields may be computed for the entire three-dimensional model. Using the computed velocity field the time-dependent advection-diffusion equations may be solved for contrast intensity in the entire three-dimensional model using a measured, calculated or assumed contrast input function. This may result in a predicted distribution of contrast throughout the three-dimensional domain that can be compared to the actual measured, and non-uniform, contrast distribution. The first set of boundary conditions may be iteratively updated and the velocity, pressure and contrast fields may be updated until the predicted contrast distribution matches the measured contrast distribution to an acceptable degree. The final updated boundary conditions may be used to compute a velocity and pressure field that is expected to be more consistent with the actual velocity and pressure fields.

Referring now to the figures, FIG. 1 depicts a block diagram of an exemplary system 100 and network for assessing the severity of plaque and/or stenotic lesions using contrast distribution predictions and measurements, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. For purposes of the disclosure, a "patient" may refer to any individual or person for whom diagnosis or treatment analysis is being performed, contrast distribution is being measured or simulated, and blood flow characteristics, blood perfusion, and the severity of plaque and/or stenotic lesions are being assessed, or any individual or person associated with the diagnosis or treatment of cardiovascular diseases or conditions, or any individual or person associated with the assessment of blood flow characteristics, blood perfusion, severity of plaque and/or stenotic lesions of one or more individuals. The physicians 102 and/or third party providers 104 may also obtain any combination of patient-specific parameters, including patient characteristics (e.g., age, medical history, etc.) and physiological and/or boundary conditions. Physicians 102 and/or third party providers 104 may transmit the anatomical images and/or patient-specific parameters to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
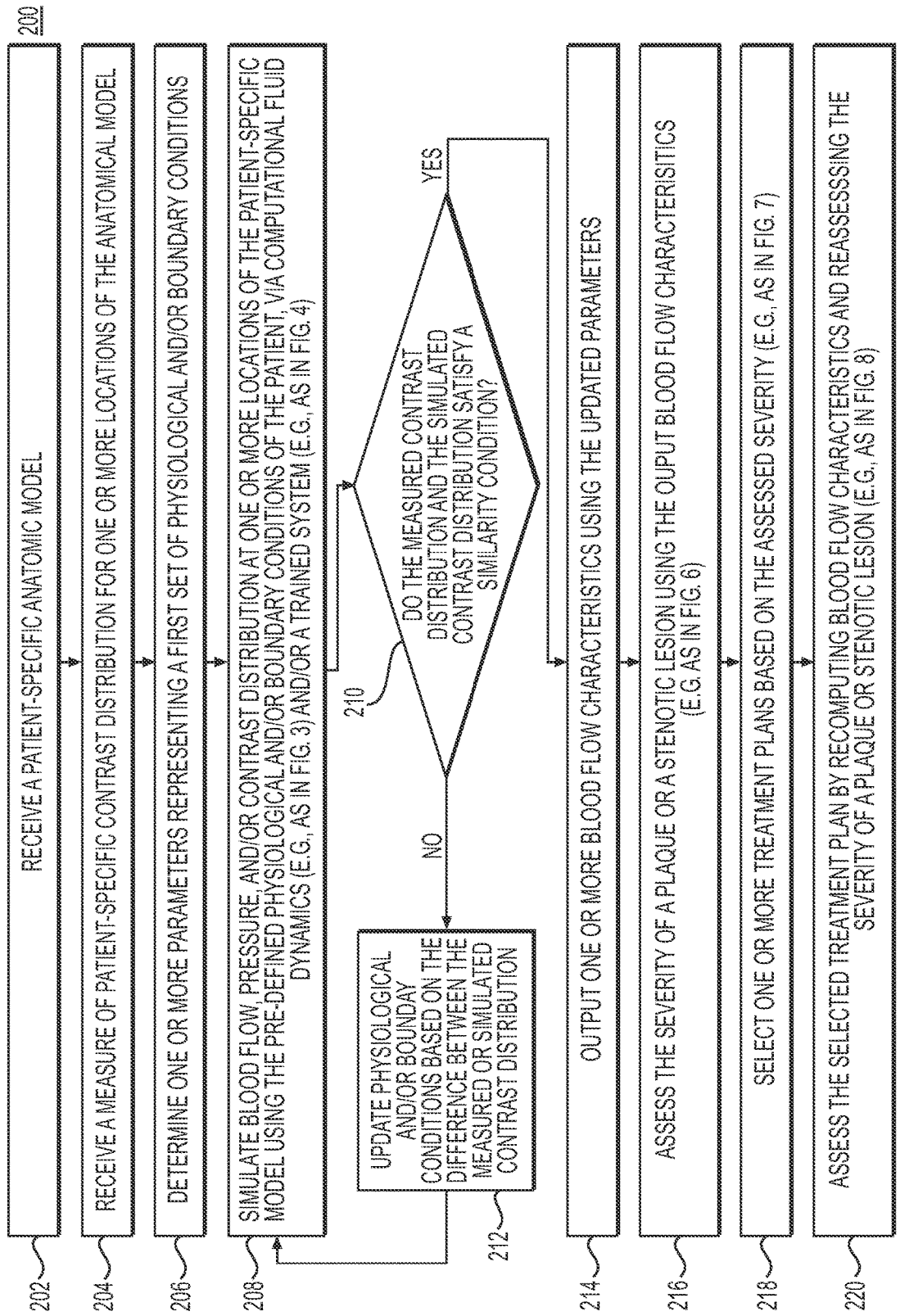
FIG. 2 is a block diagram of a general method of assessing the severity of plaque and/or stenotic lesions using contrast distribution predictions and measurements, according to an exemplary embodiment of the present disclosure.

FIG. 2 depicts a general embodiment of method 200 for assessing the severity of plaque and/or stenotic lesions using contrast distribution predictions and measurements.

In one embodiment, step 202 may include receiving a patient-specific anatomic model of the patient. The anatomic model may be constructed from image data obtained from one or more medical images of a patient, using a computational device (e.g., a computer, laptop, DSP, smart phone, etc.). Alternatively or additionally, the patient-specific anatomic model may be received from an electronic storage device (e.g., a hard drive, network drive, etc.).

Step 204 may include receiving a patient-specific contrast distribution for one or more anatomic locations represented in the patient-specific anatomic model. The contrast distribution and/or anatomic model may be in the form of one or more medical images (e.g., CT, MR, ultrasound, 3D rotational angiography, 2D angiography, etc.).

Step 206 may include determining one or more parameters to represent a first set of physiologic and/or boundary conditions of the patient for a blood flow analysis and calculation of contrast media transport. The physiological and/or boundary conditions may be assigned with initial conditions before being successively updated and/or redefined. The initial conditions for the physiological and/or boundary conditions may be defined using form-function relationships between a vascular model extracted from the patient-specific anatomic model and a population-based physiological model. Physiological conditions may include patient-specific physiological characteristics that may be measured, obtained, or derived from the patient-specific anatomic model. In one embodiment, the physiological conditions may be measured, obtained, or derived from the patient-specific anatomic model using computational fluid dynamics. The physiological characteristics may include one or more blood flow characteristics, blood pressure characteristics, baseline heart rate, height, weight, hematocrit volume, stroke volume, the geometrical and material characteristics of a vascular system, or the material characteristics of plaque and/or stenotic lesions. The boundary conditions may provide information about the anatomical model at its boundaries, e.g., the physiological relationships between variables at the boundaries of the region of interest. These boundaries may include, but are not limited to, the inflow boundaries, outflow boundaries, vessel wall boundaries, and boundaries of plaque and/or stenotic lesions. The inflow boundaries may include the boundaries through which flow is directed into the anatomy of the three-dimensional model, the outflow boundaries may include the boundaries through which flow is directed outward from the anatomy of the three-dimensional model, and the vessel wall boundaries may include the physical boundaries of the aorta, the main coronary arteries, and/or other coronary arteries or vessels of the three-dimensional model.

Step 208 may include simulating a blood flow, pressure, and contrast distribution of the patient using the defined physiologic and/or boundary conditions of the patient. Step 208 may be performed using computational fluid dynamics (CFD) and/or by using a trained system (e.g., machine learning algorithm)

Step 210 may include determining whether the received contrast distribution and the simulated contrast distribution satisfy a similarity condition. Step 210 may include comparing the received and simulated distribution of the contrast agent for one or more points or areas of the patient-specific anatomic model and noting the similarities and differences. In one embodiment, the similarity condition may be satisfied if the differences between the received contrast distribution and the simulated contrast distribution are within a specified tolerance. The specified tolerance may be received in an electronic storage medium of server systems 106 prior to step 210.

If, subsequent to step 210, the received contrast distribution and the simulated contrast distribution do not satisfy the similarity condition, step 212 may include updating the physiological and/or boundary conditions of the patient based on the comparison between the predicted contrast distribution and the actual measured contrast distribution. Subsequently, step 208 may be repeated using the updated physiological and/or boundary conditions.

The above steps of determining and/or updating one or more parameters to represent physiologic and/or boundary conditions, simulating the blood flow, pressure, and/or contrast distribution, and comparing the simulated contrast distribution and the received contrast distribution may be repeated until the simulated contrast distribution and received contrast distribution satisfy the similarity condition (e.g., the differences between the simulated contrast distribution and the received contrast distribution are within a predetermined tolerance).

If, subsequent to step 210, the received contrast distribution and the simulated contrast distribution satisfy the similarity condition, step 214 may include outputting one or more blood flow characteristics derived from the simulated contrast distribution. The output blood flow characteristics may be displayed to a user through a report or visual display, and/or may be written to an electronic storage device (e.g., hard disk, network drive, cloud storage, smart phone, tablet, etc.). In another embodiment, perfusion characteristics may be simulated in addition to, or as an alternative to, blood flow characteristics and/or contrast distribution at one or more locations on the patient-specific anatomical model. Furthermore, the perfusion characteristics may be outputted in addition to or as an alternative to blood flow characteristics.

Step 216 may include assessing the severity of a plaque or stenotic lesion using the output blood flow characteristics. In one embodiment, the severity may be assessed by determining a pressure, force, and/or strain on the plaque or stenotic lesion using the blood flow characteristics and determining the geometric and/or material characteristics of the plaque or stenotic lesion using the patient-specific anatomic model. In one embodiment, the severity of the plaque or stenotic lesion may be based on the ratio of a stress on the plaque or stenotic lesion over the strength of the plaque or stenotic lesion. The strength may be determined based on the geometric characteristic or material property of the plaque or stenotic lesion. The stress may include an acute or cumulative stress on the plaque or stenotic lesion due to a force, pressure, or strain on the plaque or stenotic lesion, which may be measured, derived, or obtained from the computed blood flow characteristics. In one embodiment, the severity of a plaque may be based on a variation of the plaque vulnerability index. The severity of a stenosis may be based on a percentage of the reduction of the cross-sectional area of a vessel due to the stenosis.

Step 218 may include selecting the appropriate treatment plans based on the computed blood flow characteristics and/or assessed severity of the plaque or stenotic lesion. In one embodiment, a suboptimal blood flow characteristic (e.g., low fractional flow reserve) and an adverse severity of a plaque or stenotic lesion (e.g., high percent stenosis or plaque strength, etc.) may be used to prescribe percutaneous coronary intervention. In another embodiment, an optimal blood flow characteristic (e.g., high fractional flow reserve) and mild severity of a plaque or stenotic lesion may be used to prescribe medical treatment. In another embodiment, a cumulative history of computed blood flow characteristics and/or severity assessments of plaque and/or stenotic lesions may be used to select the treatment options.

Figure 3:
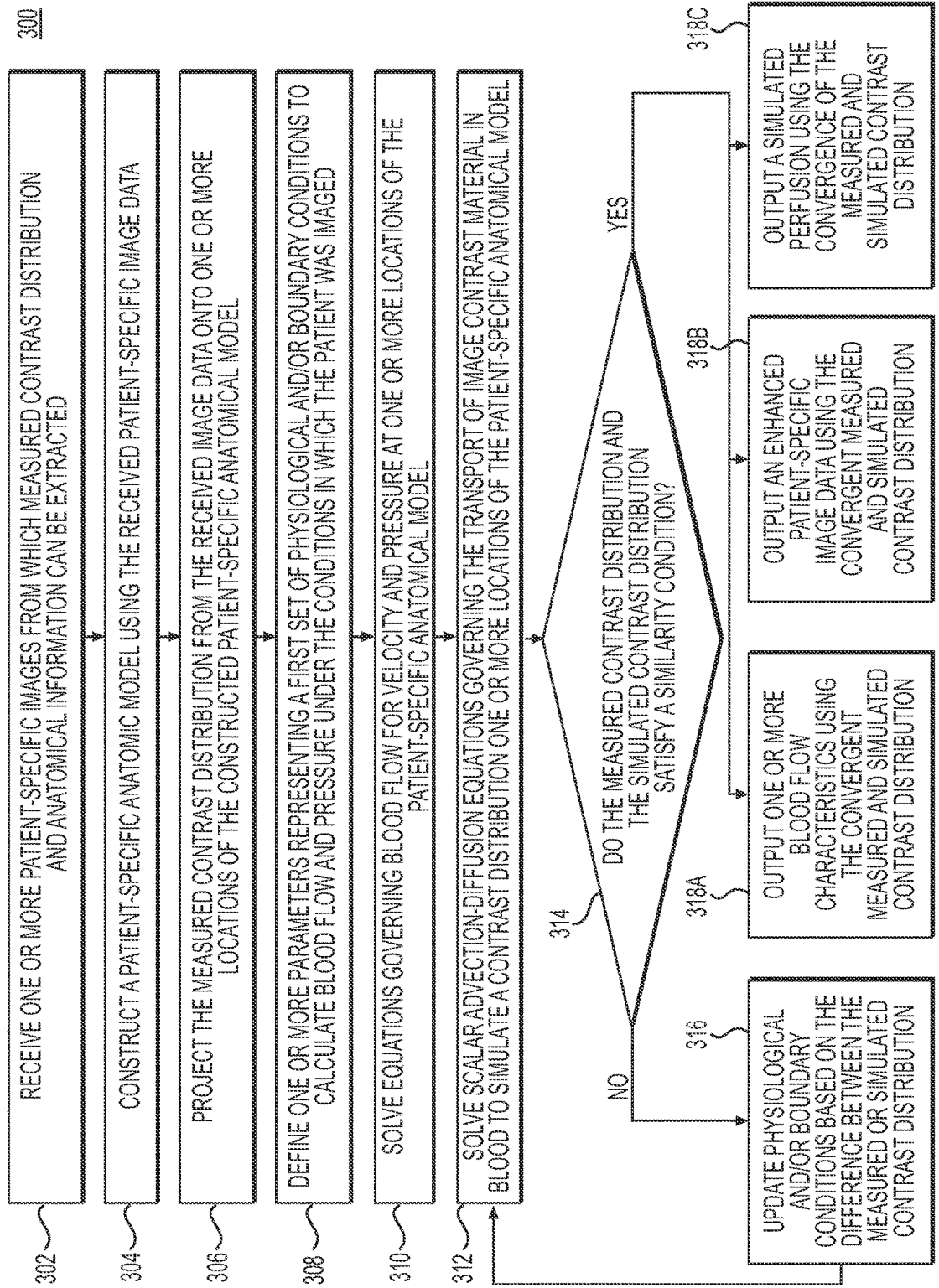
FIG. 3 is a block diagram of an exemplary method of determining blood flow characteristics, simulating perfusion, or enhancing patient-specific imaging data using contrast distribution predictions and measurements obtained from computational fluid dynamics, according to an exemplary embodiment of the present disclosure.

FIG. 3 depicts a general embodiment of method 300 for determining blood flow characteristics, simulating perfusion, or enhancing patient-specific imaging data using contrast distribution predictions and measurements obtained from computational fluid dynamics. The output from method 300 may be used for assessing the severity of a plaque or stenotic lesion, selecting the appropriate treatment plans, and/or assessing a selected treatment plan by reassessing the severity of a plaque or stenotic lesion using recomputed blood flow characteristics.

In one embodiment, step 302 may include receiving one or more patient-specific images from which measured contrast distribution and anatomical information can be extracted. The image data may be obtained from two-dimensional scans (e.g., coronary angiography, biplane angiography, etc.) or three-dimensional scans (e.g. 3D rotational angiography, coronary computed tomographic angiography (CCTA), magnetic resonance angiography (MRA), etc.).

Step 304 may include constructing a patient-specific anatomic model from the received one or more patient-specific images. This step may include methods to directly segment the image data and create a patient-specific three-dimensional anatomic model of the patient's arteries or may involve modifying a previously-constructed "generic" model to customize it for that patient and create a patient-specific model. In either case, the patient-specific anatomic model may include information related to the arteries of interest including the length of each segment, diameter along the length of a segment (or any other geometrical description of the segment), branching patterns, presence of disease, and/or characteristics of disease including composition of atherosclerotic plaque. The representation of the model may be defined by a surface enclosing a three-dimensional volume, a one-dimensional model where the centerline of the vessels is defined together with cross-sectional area information along the length or as an implicit representation of the vessel surface. The anatomic model may represent many different kinds of anatomy, such as coronary arteries, peripheral arteries, cerebral arteries, visceral arteries, hepatic vessels, renal arteries, organ tissue, heart chambers, etc. The model may also be received prior to using techniques presented herein.

Step 306 may include projecting the measured contrast distribution from the image data to the patient-specific anatomic model extracted from the image data. In the case where the anatomic model is represented using a three-dimensional domain, the contrast values may be associated with the explicit or implicit representation of the three-dimensional domain. In one embodiment, where a three-dimensional domain represents the anatomic model, there may be an assignment of contrast values for each point of the three-dimensional finite element mesh. In another embodiment, where a reduced order model (ROM) is used to represent the patient-specific anatomic model, the contrast values may be averaged over a vessel-cross-section, which may also be defined by its cross-sectional area. The contrast data may also be filtered or enhanced prior to association with the model (e.g., smoothing operators, median filtering, mean filtering, bilateral filtering, anisotropic diffusion filtering, denoising, contrast enhancement, etc., among other methods described in U.S. Pat. No. 9,070,214, issued Jun. 30, 2015, which is incorporated by reference herein in its entirety.).

Step 308 may include defining one or more parameters to represent a first set of physiological and/or boundary conditions to represent blood flow and pressure under the conditions that the patient was imaged. For example, this may involve assignment of aortic pressure conditions and resistance of the coronary artery microcirculation under conditions representing a patient in a resting or hyperemic state. For the coronary arteries, the assignment of this initial set of boundary conditions could be performed, for example, using the methods described in U.S. Pat. No. 8,315,812, issued Nov. 20, 2012, which is incorporated by reference herein in its entirety. In one embodiment, step 308 may also require assigning an initial contrast distribution in the patient-specific anatomic model.

Step 310 may include solving the equations governing blood flow for velocity and pressure. In one embodiment, step 310 may include the computing of a blood flow velocity field or flow rate field that will advect the contrast and pressure field for one or more points or areas of the anatomic model, using the assigned boundary conditions. This velocity field or flow rate field may be the same field as computed by solving the equations of blood flow using the physiological and/or boundary conditions provided above.

Step 312 may include solving scalar advection-diffusion equations governing the transport of image contrast material in blood to simulate the contrast distribution at one or more locations of the patient-specific anatomic model. These advection-diffusion equations may involve using the blood flow velocity field advecting the contrast and pressure fields of the patient-specific anatomic model computed in step 310. The solutions to the equations of steps 310 and 312 may require input related to the diffusivity of the contrast in blood, which may be obtained from literature data or measurements.

The computation of contrast distribution may also require assignment of an initial contrast distribution for step 308, which would typically be zero contrast media in the patient-specific anatomic model as well as assignment of boundary conditions in step 308 related to the contrast intensity of flux of contrast at the input of the patient-specific domain, along the vessel walls and at the outlets of the three-dimensional computational domain. In one embodiment, the vessel walls may be assumed to be insulating, i.e. zero contrast flux through the vessel walls, whereas at the outlet boundaries, it may be assumed that the contrast is free to transport out of the three-dimensional anatomic model. Thus, a transport boundary condition at the inlet (e.g. aortic input or at the coronary ostia for coronary blood flow simulations) may be assigned to the patient-specific domain. For coronary blood flow simulations, this may be referred to as the aortic input function (AIF), whereas for other vascular beds, the conditions in the aorta may be less relevant so this may be referred to as a contrast input function (CIF) for the most general case. The CIF may be obtained from measurements or the form of the CIF can be assumed to be represented by known or initially unknown parameter values. Given a patient population with a known CIF, the CIF of the most similar patient may also be used.

Step 314 may include determining whether the simulated contrast distribution from step 312 and the actual received contrast distribution satisfy a similarity condition. Step 314 may include comparing the received and simulated distribution of the contrast agent for one or more points or areas of the patient-specific anatomic model and noting the similarities and differences. In one embodiment, the similarity condition may be satisfied if the differences between the received contrast distribution and the simulated contrast distribution are within a specified tolerance. The specified tolerance may be received in an electronic storage medium of server systems 106 prior to step 314.

If, subsequent to step 314, the received contrast distribution and the simulated contrast distribution do not satisfy the similarity condition, step 316 may include updating the physiologic and/or boundary conditions of the patients based on the comparison between the predicted contrast distribution and the actual measured contrast distribution. The iterative update may be done using either derivative-free or gradient-based methods. In the former, the cost function may be calculated using techniques like the Nelder-Mead method which operates by approximating the cost function as simplexes in the parameter space and sequentially updating the vertices of the simplex based on the cost function. Moreover, sequential derivative-free approaches based on nonlinear ensemble filtering may iteratively adjust parameters "on-the-fly" and may be practical for computationally expensive distributed mechanical models. Alternatively, gradients of the cost function with respect to parameters may be estimated using techniques such as finite difference, by linearizing the partial differential equations with respect to the parameters, or via the adjoint method. Parameters may be updated by incrementing along the direction of the negative gradient. Subsequently, step 312 may be repeated using the updated physiological and/or boundary conditions.

If, subsequent to step 314, the received contrast distribution and the simulated contrast distribution satisfy the similarity condition then the iterative process is complete and the solution deemed converged.

Step 318A may include outputting the blood flow characteristics for one or more locations on the patient-specific anatomic model from the converged solution. The blood flow characteristics may include, but are not limited to, the computed velocity, pressure, FFR, coronary flow reserve (CFR), shear stress, axial plaque stress, etc.

In one embodiment, step 318B may include using the computed contrast distribution from the converged solution of step 314 to enhance the initial image data that had been received in step 302. For example, the image data may be enhanced by replacing the pixel values with the simulated contrast values. In another example, the simulated contrast values may be used to "de-noise" the original image via a conditional random field. Step 318B may further include outputting the enhanced medical image.

In one embodiment, step 318C may include using the computed blood flow characteristics associated with the converged contrast distribution solution to determine an appropriate perfusion data for one or more points, areas, or regions of the patient-specific anatomic model. Furthermore, the perfusion data may be used to generate a model or medical image simulating the perfusion of a tissue, organ, and/or vascular network. Step 318C may be used to improve the methods described in U.S. Pat. No. 8,386,188 issued Feb. 26, 2013, and U.S. Pat. No. 8,315,814 issued Nov. 20, 2012, directed to simulating perfusion in the heart and brain, respectively, which are incorporated by reference herein in their entireties. Step 318C may further include outputting the perfusion data or using the perfusion data to output an enhanced medical image.

Steps 318A, 3188, and 318C may be performed by a processor individual or in a combination thereof. The outputs may be stored in an electronic storage medium and/or displayed.

Figure 4:
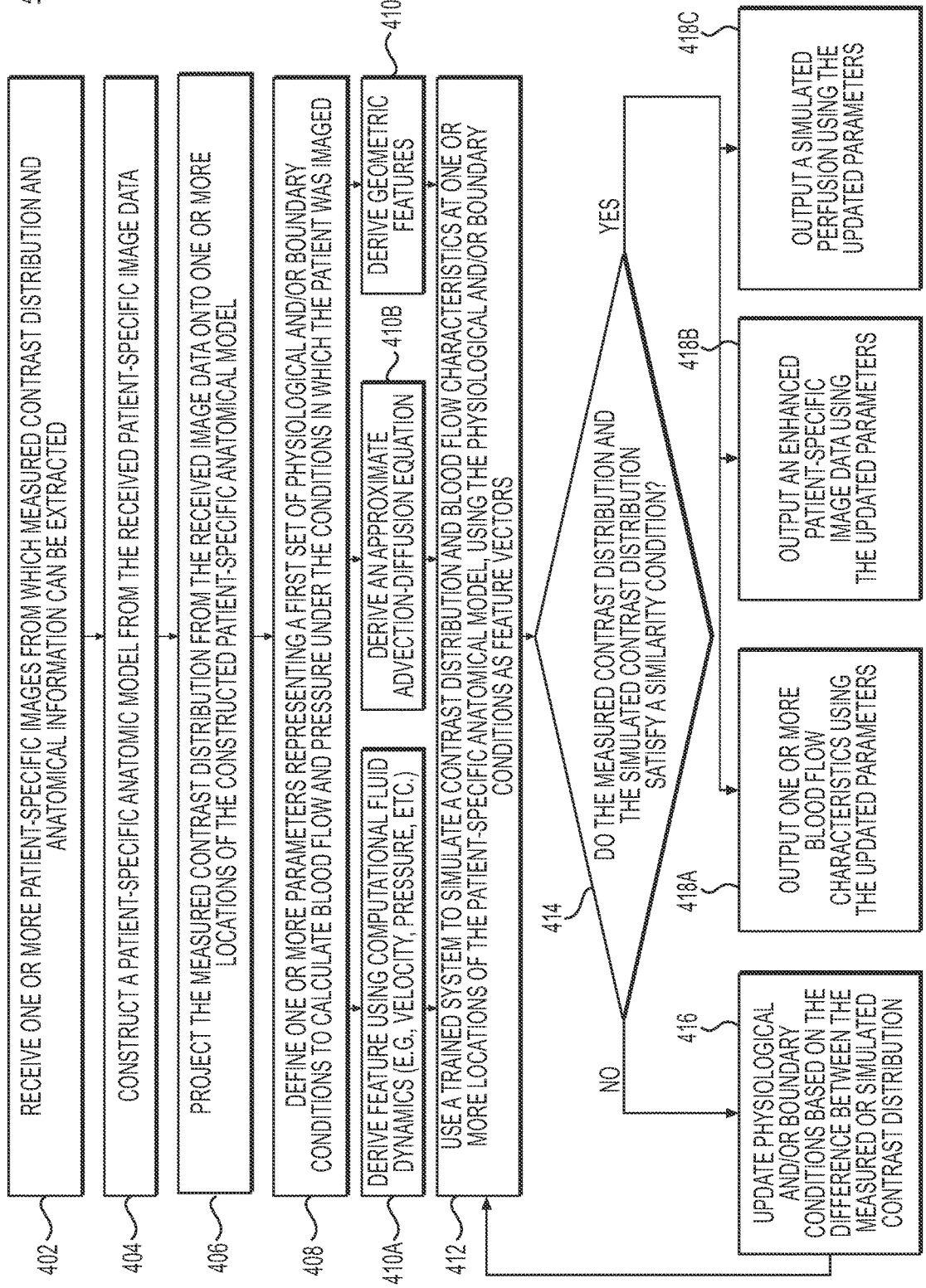
FIG. 4 is a block diagram of an exemplary method of determining blood flow characteristics, simulating perfusion, or enhancing patient-specific imaging data using contrast distribution predictions and measurements obtained from a trained system, according to an exemplary embodiment of the present disclosure.

FIG. 4 depicts a general embodiment of method 400 for determining blood flow characteristics, simulating perfusion, or enhancing patient-specific imaging data using contrast distribution predictions and measurements obtained from a trained system, according to an exemplary embodiment of the present disclosure. The output from method 400 may be used for assessing the severity of a plaque or stenotic lesion (e.g. as in method 600), selecting appropriate treatment options (e.g. as in method 700), and/or assessing a selected treatment plan by reassessing the severity of a plaque or stenotic lesion using recomputed blood flow characteristics.

In one embodiment, step 402 may include receiving one or more patient-specific images from which measured contrast distribution and anatomical information can be extracted. The image data may be obtained from two-dimensional scans (e.g., coronary angiography or biplane angiography for a coronary anatomy) or three-dimensional scans (e.g. 3D rotational angiography, coronary computed tomographic angiography (CCTA), or magnetic resonance angiography (MRA) for a coronary anatomy).

Step 404 may include constructing a patient-specific anatomic model from the received one or more patient-specific images. This step may include methods to directly segment the image data and create a patient-specific three-dimensional anatomic model of the patient's arteries or may involve modifying a previously-constructed "generic" model to customize it for that patient and create a patient-specific model. In either case, the patient-specific anatomic model may include information related to the arteries of interest including the length of each segment, diameter along the length of a segment (or any other geometrical description of the segment), branching patterns, presence of disease, and/or characteristics of disease including composition of atherosclerotic plaque. The representation of the model may be defined by a surface enclosing a three-dimensional volume, a one-dimensional model where the centerline of the vessels is defined together with cross-sectional area information along the length or as an implicit representation of the vessel surface. The anatomic model may represent many different kinds of anatomy, such as coronary arteries, peripheral arteries, cerebral arteries, visceral arteries, hepatic vessels, renal arteries, organ tissue, heart chambers, etc. The model may also be received prior to using techniques presented herein.

Step 406 may include projecting the measured contrast distribution from the image data to the patient-specific anatomic model extracted from the image data. In the case where the anatomic model is represented using a three-dimensional domain, the contrast values may be associated to the explicit or implicit representation of this domain. In one embodiment, where a three-dimensional domain represents the anatomic model, there may be an assignment of contrast values for each point of the three-dimensional finite element mesh. In another embodiment, where a reduced order model (ROM) is used to represent the patient-specific anatomic model, the contrast values may be averaged over a vessel-cross-section, which may also be defined by its cross-sectional area. The contrast data may also be filtered or enhanced prior to association with the model (e.g., smoothing operators, median filtering, mean filtering, bilateral filtering, anisotropic diffusion filtering, de-noising, contrast enhancement, etc., among other methods described in U.S. Pat. No. 9,070,214 issued Jun. 30, 2015, which is incorporated by reference herein in its entirety).

Step 408 may include defining one or more parameters to represent a first set of physiological and/or boundary conditions to represent blood flow and pressure under the conditions that the patient was imaged. For example, this may involve assignment of aortic pressure conditions and resistance of the coronary artery microcirculation under conditions representing a patient in a resting or hyperemic state. For the coronary arteries, the assignment of the first set of boundary conditions could be performed, for example, using the methods described in U.S. Pat. No. 8,315,812 issued Nov. 20, 2012, which is incorporated by reference herein in its entirety. In one embodiment, the one or more parameters representing the physiological and/or boundary conditions may be divided into classes, which may include, but are not limited to, (i) CFD-derived features such as flow velocity and pressure, (ii) analytical approximation of the advection-diffusion equation, and (iii) geometric features such as minimum lumen diameter of the stenosis, length of stenosis.

For example, step 410A may include defining parameters representing physiological and/or boundary conditions derived from computational fluid dynamics (e.g., blood flow velocity and pressure), step 410B may include defining parameters representing an analytical approximation of the advection-diffusion equation, and step 410C may include defining parameters representing geometric features of the points or areas of the patient-specific anatomic model where the CFD-derived features and advection-diffusion equation have been computed. In one embodiment, other classes of features (e.g. patient-specific dispersitivity) may also be used.

Step 412 may include using a trained system to simulate a contrast distribution at one or more locations on the patient-specific anatomic model, using the parameters representing physiological and/or boundary conditions, advection-diffusion equation, and geometric features as feature vectors. In one embodiment, step 412 may include the use of machine learning to compute the blood flow characteristic as well as the contrast distribution, using, for example, the methods described in U.S. patent application Ser. No. 13/895,893 filed May 16, 2013, which is incorporated by reference herein in its entirety. Method 500 of FIG. 5 may provide a detailed embodiment of step 412 of method 400.

Step 414 may include determining whether the simulated contrast distribution from step 412 and the actual received contrast distribution satisfy a similarity condition. Step 414 may include comparing the received and simulated distribution of the contrast agent for one or more points or areas of the patient-specific anatomic model and noting the similarities and differences. In one embodiment, the similarity condition may be satisfied if the differences between the received contrast distribution and the simulated contrast distribution are within a specified tolerance. The specified tolerance may be received in an electronic storage medium of server systems 106 prior to step 414.

If, subsequent to step 414, the received contrast distribution and the simulated contrast distribution do not satisfy the similarity condition, step 416 may include updating the physiologic and/or boundary conditions of the patients based on the comparison between the predicted contrast distribution and the actual measured contrast distribution. In one embodiment, one way of updating physiologic boundary conditions resulting in matching between the predicted and measured contrast distribution could be achieved by defining three broad classes of features and computing a map between these and the contrast concentration along the vessels. The three broad classes of features may include (i) CFD-derived features such as flow velocity and pressure, (ii) analytical approximation of the advection-diffusion equation, and (iii) geometric features such as minimum lumen diameter of the stenosis, length of stenosis etc. (all features in the '893 application referenced above can be used). A system can be trained (on a set of training data that includes measured or simulated contrast distributions as well as anatomic models) that maps these features to contrast concentration along centerlines. Other classes of features (e.g. patient-specific dispersitivity) may also be used. During optimization, the machine learning approximation may be used instead of solving both the Navier-Stokes equations and the advection-diffusion equations.

If, subsequent to step 414, the received contrast distribution and the simulated contrast distribution satisfy the similarity condition, then the iterative process is complete and the solution deemed converged.

Step 418A may include outputting the blood flow characteristics for one or more locations on the patient-specific anatomic model from the converged solution. The blood flow characteristics may include, but are not limited to, the computed velocity, pressure, FFR, coronary flow reserve (CFR), shear stress, axial plaque stress, etc.

In one embodiment, step 418B may include using the computed contrast distribution from the converged solution of step 414 to enhance the initial image data that had been received in step 402. For example, the image data may be enhanced by replacing the pixel values with the simulated contrast values. In another example, the simulated contrast values may be used to "de-noise" the original image via a conditional random field. Step 418B may further include outputting the enhanced medical image.

In one embodiment, step 418C may include using the computed blood flow characteristics associated with the converged contrast distribution solution to determine an appropriate perfusion data for one or more points, areas, or regions of the patient-specific anatomic model. Furthermore, the perfusion data may be used to generate a model or medical image simulating the perfusion of a tissue, organ, and/or vascular network. Step 418C may be used to improve the methods described in U.S. Pat. Nos. 8,386,188 and 8,315,814 directed to simulating perfusion in the heart and brain, respectively, which are incorporated by reference herein in their entireties. Step 418C may further include outputting the perfusion data or using the perfusion data to output an enhanced medical image.

Steps 418A, 418B, and 418C may be performed by a processor individual or in a combination thereof. The outputs may be stored in an electronic storage medium and/or displayed.

Figure 5:
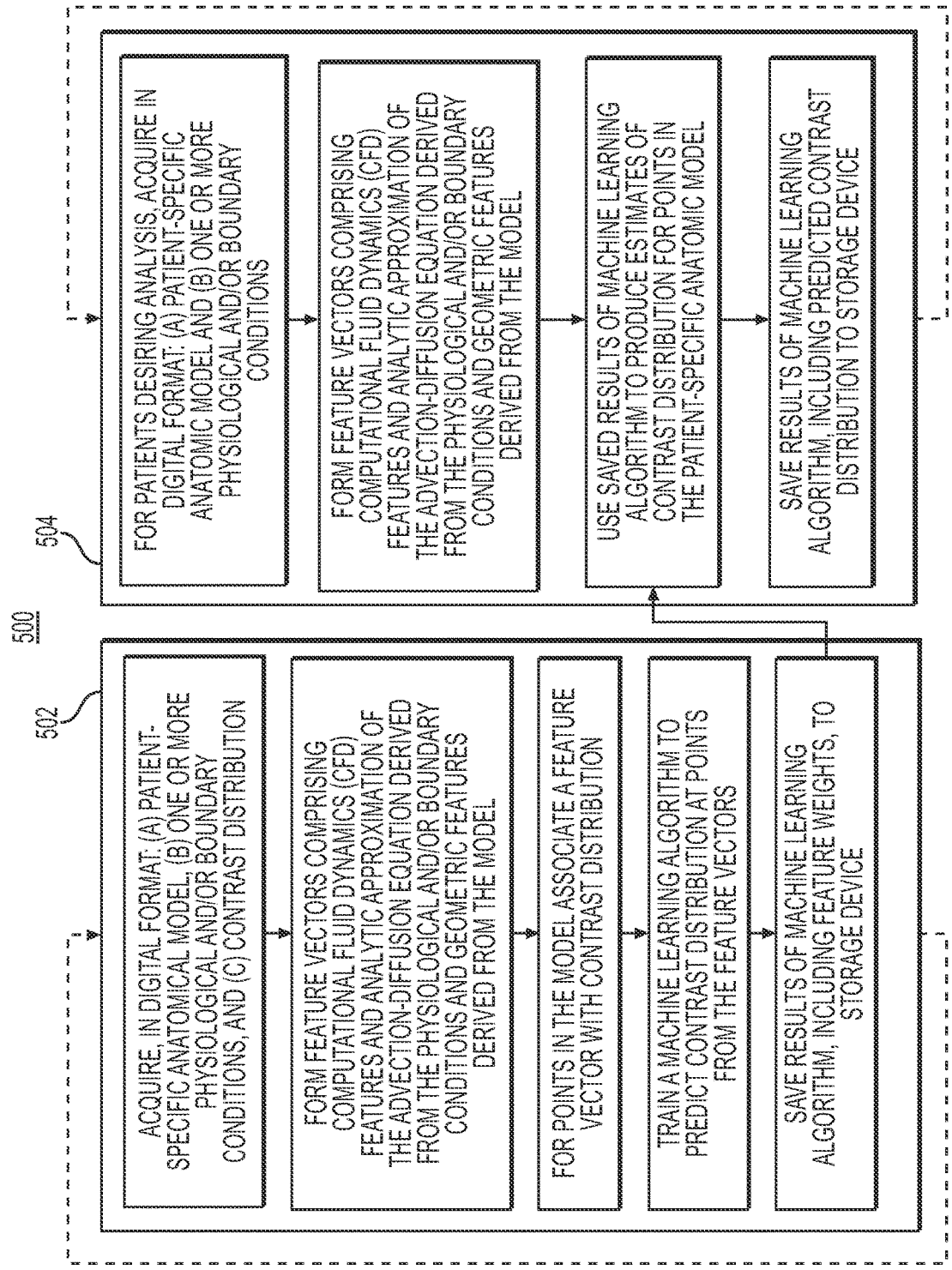
FIG. 5 is a block diagram of an exemplary method of training and applying a machine learning algorithm using a patient-specific anatomic model and physiological and/or boundary conditions to output a contrast distribution in the anatomical model, according to an exemplary embodiment of the present disclosure.

FIG. 5 is a block diagram of an exemplary method of training and applying a machine learning algorithm using a patient-specific anatomic model and physiological and/or boundary conditions to output a contrast distribution in the anatomical model, according to an exemplary embodiment of the present disclosure. FIG. 5 may include an exemplary method of performing steps 412 of method 400 in FIG. 4. The method 500 of FIG. 5 may be performed by server systems 106, based on information received from physicians 102 and/or third party providers 104 over electronic network 100.

In one embodiment, the method 500 of FIG. 5 may include a training method 502, for training one or more machine learning algorithms based on patient-specific parameters from numerous patients and measured, estimated, and/or simulated blood flow and/or blood supply demand characteristics, and a production method 504 for using the machine learning algorithm results to predict the blood flow and/or blood supply demand characteristics of an intended transplant recipient or donor.

In one embodiment, training method 502 may involve acquiring, for each of a plurality of individuals, e.g., in digital format: (a) a patient-specific anatomical model, (b) one or more measured or estimated physiological and/or boundary conditions, and (c) estimated or simulated contrast distribution. Training method 502 may then involve, for one or more points in each patient's model, creating a feature vector comprising of features derived from computational fluid dynamics, features of the analytic approximation of the advection-diffusion equation derived from the physiological and/or boundary conditions, and geometric features derived from the anatomical model. Training method 502 may further include associating the feature vector with the contrast concentration or distribution at those points of the anatomical model. Training method 502 may then save the results of the machine learning algorithm, including feature weights, in a storage device of server systems 106. The stored feature weights may define the extent to which patient-specific parameters and/or anatomical location are predictive of contrast concentration and/or distribution.

In one embodiment, the production method 504 may involve estimating the contrast concentration and/or distribution for a particular patient, based on results of executing training method 502. In one embodiment, production method 504 may include acquiring, e.g. in digital format: (a) a patient-specific anatomical model, and (b) one or more physiological and/or boundary conditions. For multiple points in the patient's anatomical model, production method 504 may involve creating a feature vector of features derived from computational fluid dynamics, features of the analytic approximation of the advection-diffusion equation derived from the physiological and/or boundary conditions, and geometric features derived from the anatomical model. The types of features used in the production mode may be the same as the types of features used in the training mode. Production method 504 may then use saved results of the machine learning algorithm to produce estimates of the patient's contrast concentration and/or distribution for the multiple points of the patient-specific anatomic model. Finally, production method 504 may include saving the results of the machine learning algorithm, including predicted contrast concentration and/or distribution, to a storage device of server systems 106.

Figure 6:
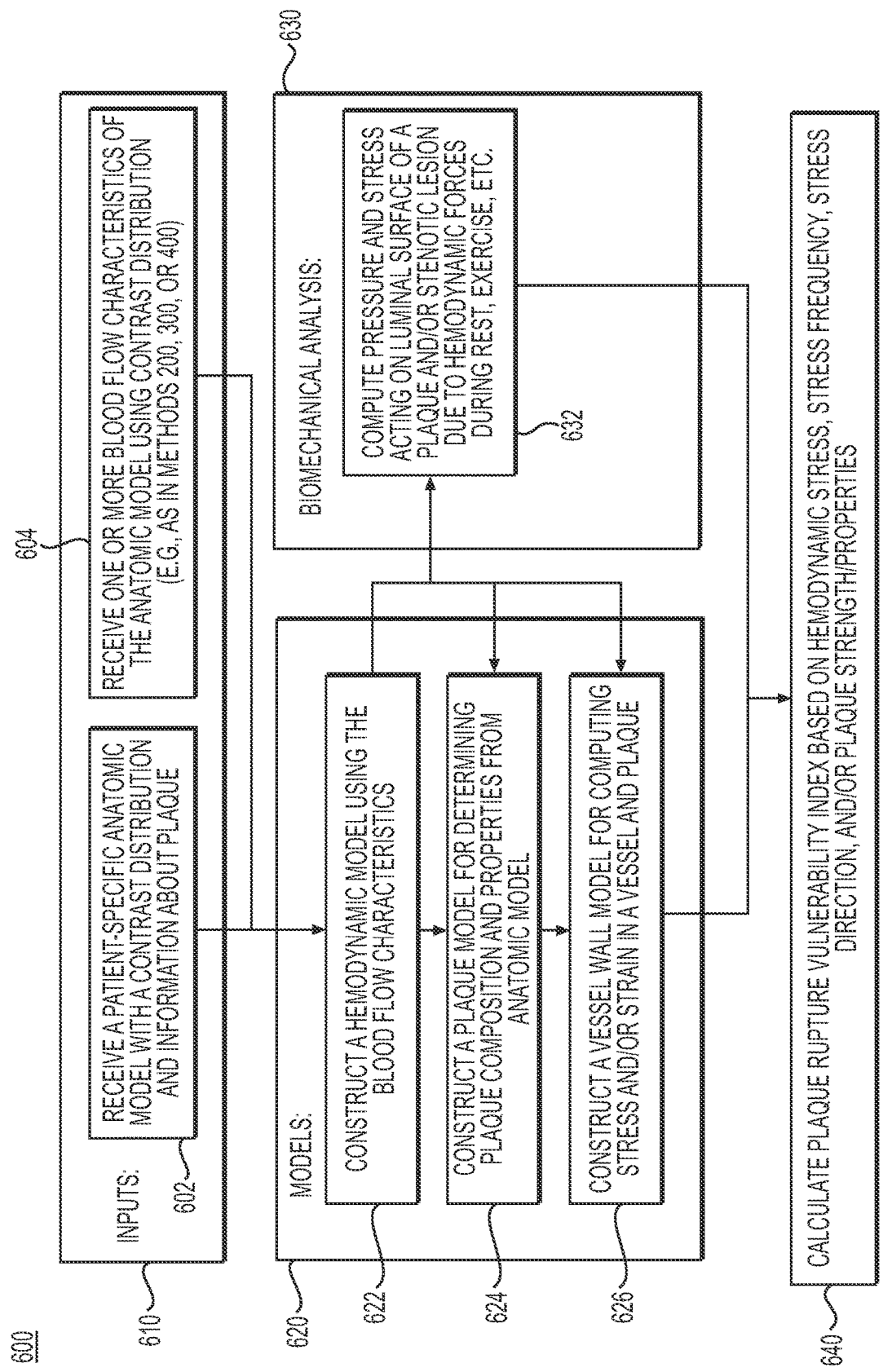
FIG. 6 is a block diagram of an exemplary method of using patient-specific contrast distribution of a patient-specific anatomic model to assess the severity of a plaque or stenotic lesion, according to an exemplary embodiment of the present disclosure.

While methods 200, 300, 400, and 500 may result in systems and methods of determining blood flow characteristics using simulated and measured contrast distribution, the embodiments presented in method 600 of FIG. 6 may utilize the improved calculation of blood flow and pressure to better assess the severity of stenotic lesions or to improve the prediction of plaque rupture, as for example described in U.S. Pat. No. 8,311,748 issued Nov. 13, 2012, which is incorporated by reference herein in its entirety. The embodiments of this disclosure result in more accurate predictions of baseline conditions that could then be used in treatment planning for example as described in U.S. Pat. No. 8,157,742 issued Apr. 17, 2012, U.S. Pat. No. 8,594,950 issued Nov. 26, 2013, and U.S. Pat. No. 8,734,357 issued May 27, 2014, which are incorporated by reference herein in their entireties.

FIG. 6 is a block diagram showing aspects of an exemplary method 600 of using patient-specific contrast distribution of a patient-specific anatomic model to assess severity of a plaque and/or a stenotic lesion, according to an exemplary embodiment of the present disclosure. FIG. 6 may include an exemplary method of performing step 216 of method 200 in FIG. 2. Method 600 may be performed using a processor of server systems 106 and may include generating one or more models 620 using one or more inputs 610, performing one or more biomechanical analyses 630 based on the one or more of the models 620, and providing various results based on the models 620 and the biomechanical analyses 630.

The inputs 610 may include a patient-specific anatomic model with a contrast distribution, and plaque and/or one or more stenotic lesions and may also include one or more blood flow characteristics measured, derived, or obtained using the methods 200, 300, 400, or 500, as described in FIGS. 2, 3, and 4, respectively. In one embodiment, steps 602 and/or step 604 may be performed to receive the inputs for method 600. Step 602 may include receiving a patient-specific anatomic model with a contrast distribution and plaque and/or one or more stenotic lesions. The anatomic model may be constructed using patient-specific image data, from which contrast distribution and anatomical information may be extracted and projected on to the anatomic model (e.g., as in steps 306 and 406 of methods 300 and 400, respectively). The image data may be obtained from two-dimensional scans (e.g., coronary angiography, biplane angiography, etc.) or three-dimensional scans (e.g. 3D rotational angiography, coronary computed tomographic angiography (CCTA), magnetic resonance angiography (MRA), etc.). The anatomic model may include information related to the arteries of interest including the length of each segment, diameter along the length of a segment (or any other geometrical description of the segment), branching patterns, presence of stenoses, lesions, plaque, occlusions, disease, and/or characteristics of disease including composition of atherosclerotic plaque. The representation of the model may be defined by a surface enclosing a three-dimensional volume, a one-dimensional model where the centerline of the vessels is defined together with cross-sectional area information along the length, or as an implicit representation of the vessel surface.

Step 604 may include receiving one or more blood flow characteristics of the anatomic model using contrast distribution. In one embodiment step 604 may be performed by receiving the output of methods 200, 300, 400 (e.g., by iteratively comparing the simulated contrast distribution to received contrast distribution). The blood flow characteristics may include, but are not limited to, a computed velocity, blood pressure, heart rate, FFR, coronary flow reserve (CFR), shear stress, axial plaque stress, etc. The inputs 610 of the patient-specific anatomic model and/or one or more blood flow characteristics may be used to generate the models 620 and/or perform the biomechanical analyses 630 described below.

As noted above, one or more models 620 may be generated based on the inputs 610. For example, step 622 may include constructing a hemodynamic model using the received blood flow characteristics at one or more locations of the patient-specific anatomic model. In one embodiment, the hemodynamic model may be created by overlaying the received one or more blood flow characteristics on the received patient-specific anatomic model. The hemodynamic model may be a simulated blood pressure model, a simulated blood flow model, or other simulation produced after performing a computational fluid dynamics analysis, e.g., as described in step 310 of FIG. 3. Solid mechanics models, including fluid structure interaction models, may be solved with the computational analysis with known numerical methods.

Method 600 may include performing a biomechanical analysis 630 using the one or more models 620. For example, step 632 may include computing a pressure and shear stress acting on the luminal surface of a plaque and/or stenosis due to hemodynamic forces at various physiological states, such as rest, varying levels of exercise or exertion, etc. The pressure and shear stress may be calculated based on information from the hemodynamic model 622, e.g., blood pressure and flow. Step 632 may include identifying one or more locations of a plaque and/or a stenosis in order to compute the pressure and shear stress.

Method 600 may also include generating models, in addition to the hemodynamic model, in order to assess the severity of a plaque and/or stenosis. In one embodiment, step 624 may include constructing a plaque model for determining plaque composition and properties from the anatomic model. The plaque model may include information regarding density and other material properties of the plaque. The plaque model may include information regarding stress and strain, which may be calculated based on the plaque composition and properties and the pressure and shear stress calculated in step 632. In one embodiment, step 632 may include performing a biomechanical analysis 630 using the plaque model (e.g., computing the stress or force on a plaque or stenotic lesion due to hemodynamic forces based on information from the plaque model).

In one embodiment, step 626 may include constructing a vessel wall model for computing information about the plaque, the vessel walls, and/or the interface between the plaque and the vessel walls. The vessel wall model may include information regarding stress and strain, which may be calculated based on the plaque composition and properties included in the plaque model and the pressure and shear stress calculated in step 632. In one embodiment, step 632 may include performing a biomechanical analysis 630 using the vessel wall model (e.g., computing the stress or force on a plaque or stenotic lesion due to hemodynamic forces based on information from the vessel wall model).

In one embodiment, step 640 may include calculating a plaque rupture vulnerability index to assess the severity of a plaque and/or stenosis. The plaque rupture vulnerability index may be calculated based on, one or more of, hemodynamic stress, stress frequency, stress direction, and/or plaque strength or other properties. In one embodiment. Performing step 640 may include isolating the region surrounding a plaque of interest from the plaque model and/or anatomic model. The severity of the plaque and/or stenosis may be determined from the material properties provided in the plaque model 624. A hemodynamic and tissue stress on the plaque of interest, due to pulsatile pressure, flow, and neck motion, may be calculated under simulated baseline and exercise (or exertion) conditions by using the hemodynamic stresses and motion-induced strains previously computed in step 634. The vulnerability of the plaque and/or stenotic lesion may be assessed based on the ratio of plaque stress to plaque strength. Step 640 may be performed by a processor of server systems 106.

While methods 200, 300, 400, 500, and 600 may describe embodiments related to more accurately computing blood flow and pressure in the human coronary arteries and/or using the improved calculation of blood flow and pressure to better assess the severity of plaque and/or stenotic lesions, the same methods may be used for other embodiments include computing blood flow and pressure in and/or using the assessing the severity of plaque and/or stenotic lesions in the extracranial and intracranial cerebral arteries, the lower extremity arteries including the iliac, superficial femoral, common femoral, tibial, popliteal, peroneal, pedal arteries in patients with peripheral arterial disease, the renal arteries, the mesenteric arteries and other vascular beds.

Figure 7:
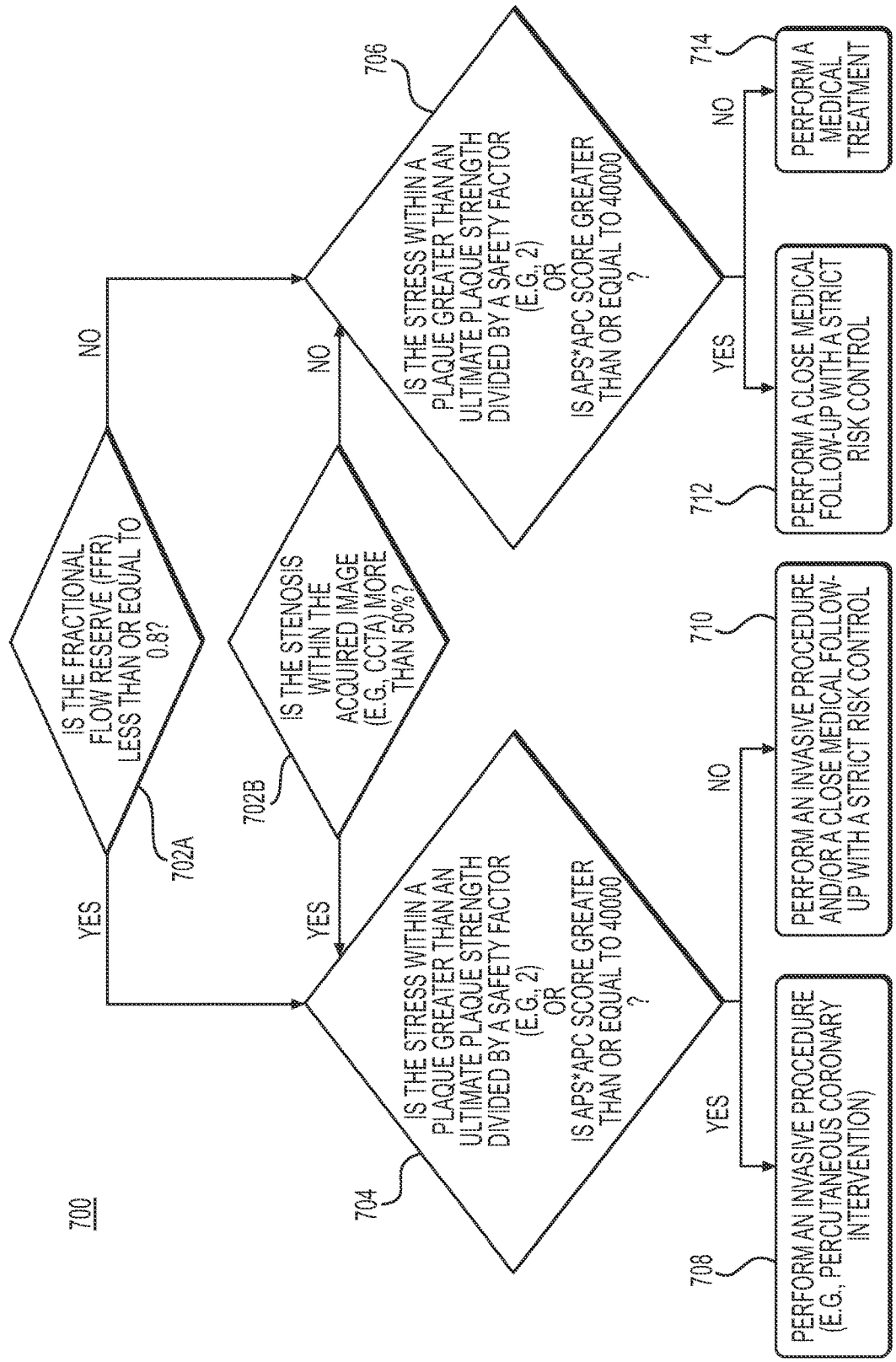
FIG. 7 is a block diagram of an exemplary method of using blood flow characteristics and/or assessments of the severity of plaque and/or stenotic lesions to select appropriate treatment plans.

FIG. 7 is block diagram of exemplary method, 700 for using blood flow characteristics obtained from methods 200, 300, 400, and 500 and/or assessments of the seventy of plaque and/or stenotic lesions obtained from method 600 to select one or more appropriate treatment plans, according to an exemplary embodiment of the present disclosure. Moreover, FIG. 7 depicts embodiments for performing step 218 of selecting treatment plans based on the saved blood flow characteristics and/or assessments of the severity of plaque and/or stenotic lesions. In one embodiment, step 702A may include determining whether the fractional flow reserve (FFR) value of the patient is less than or equal to a threshold for fractional flow reserve values (e.g., 0.8). The fractional flow reserve of the patient may be obtained, measured, or derived from the electronic storage medium and/or by using methods 200, 300, 400, or 500, disclosed in the present disclosure, which provide systems and methods for determining blood flow characteristics, including fractional flow reserve values of a patient-specific anatomic model, using simulated and measured contrast distribution. As an alternative or an addition to step 702A, step 702B may include determining whether a stenosis within the patient-specific anatomic model or image data is more than 50%. Information about the stenosis of the patient may be obtained, measured, or derived from the patient-specific anatomic model or image data, or by the assessing the severity of a stenotic lesion, as in method 600. In one embodiment, information about the stenosis may be obtained, measured or derived from an enhanced medical image or model generated from the blood flow characteristics obtained using the methods of 200, 300, or 400.

If, subsequent to steps 702A and/or 702B, the fractional flow reserve (FFR) value of the patient is less than or equal to the threshold for fractional flow reserve values. e.g., 0.8, or, alternatively or additionally, the stenosis within the patient-specific anatomic model or image data is more than 50%, then step 704 may be performed. In one embodiment, step 704 may include determining whether the stress within a plaque is greater than an ultimate plaque strength divided by a safety factor (e.g., of two) or whether the axial plaque stress multiplied by the atherosclerotic plaque characteristics (APC) score is greater than or equal to a threshold for the product value (e.g., 40,000).

If, subsequent to step 704, either the stress within a plaque is greater than an ultimate plaque strength divided by a safety factor (e.g., of two) or the axial plaque stress (APS) multiplied by the atherosclerotic plaque characteristics (APC) score is greater than or equal to the threshold for the product value (e.g., 40,000), then step 708 may include performing an invasive procedure on the patient to treat the plaque or stenotic lesion. In one embodiment, this invasive procedure may be a percutaneous coronary intervention (PCI). If, subsequent to step 704, neither the stress within a plaque is greater than an ultimate plaque strength divided by a safety factor (e.g. 2) nor is the axial plaque stress (APS) multiplied by the atherosclerotic plaque characteristics (APC) score greater than or equal to the threshold for the product value (e.g., 40,000), then step 710 may include performing an invasive procedure (e.g., percutaneous coronary intervention (PCI)) on the patient or performing close medical follow-up with a strict risk control. In one embodiment, step 710 may be performed to treat a medical condition that may not be as severe as the medical condition for which step 708 is performed.

If, subsequent to steps 702A and/or 702B, the fractional flow reserve (FFR) value of the patient is greater than the threshold for fractional flow reserve values, e.g., 0.8, or, alternatively or additionally, the stenosis within the patient-specific anatomic model or image data is less than 50%, then step 706 may be performed.

Like step 704, step 706 may include determining whether the stress within a plaque is greater than an ultimate plaque strength divided by a safety factor (e.g., of two) or whether the axial plaque stress multiplied by the atherosclerotic plaque characteristics (APC) score is greater than or equal to a threshold for the product value (e.g., 40,000). If, subsequent to step 706, either the stress within a plaque is greater than an ultimate plaque strength divided by a safety factor (e.g. 2) or the axial plaque stress (APS) multiplied by the atherosclerotic plaque characteristics (APC) score is greater than or equal to the threshold for the product value (e.g., 40,000), then step 712 may include performing an invasive procedure (e.g., percutaneous coronary intervention (PCI)) on the patient or a close medical follow-up with a strict risk control. In one embodiment, step 712 may be performed to treat a medical condition that may not be as severe as the medical condition for which step 708 is performed. If, subsequent to step 706, neither a stress within a plaque is greater than an ultimate plaque strength divided by a safety factor (e.g., 2) nor is the axial plaque stress (APS) multiplied by the atherosclerotic plaque characteristics (APC) score greater than or equal to the threshold for the product value (e.g., 40,000), then step 714 may include performing a medical treatment. In one embodiment, step 714 may be performed to treat a medical condition that may not be as severe as the medical conditions for which step 708, 710, or 712 are performed.

Figure 8:
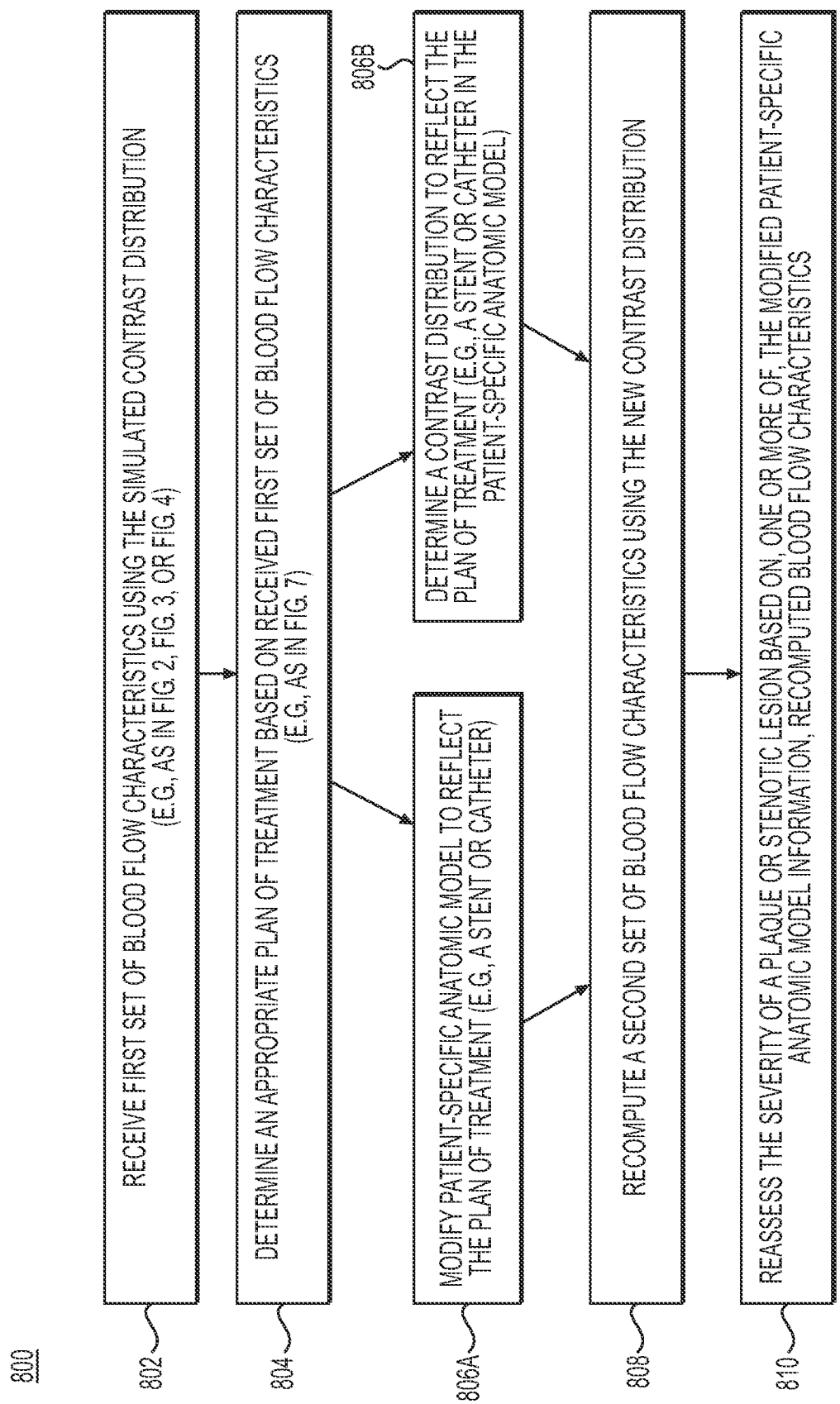
FIG. 8 is a block diagram of an exemplary method of assessing a selected treatment plan by reassessing the severity of plaque and/or stenotic lesions using recomputed blood flow characteristics.

FIG. 8 is a block diagram of exemplary method 800 for assessing a selected treatment plan (e.g., as selected using method 700 of FIG. 7) by reassessing the severity of plaque and/or stenotic lesions (e.g., as described in method 600 of FIG. 6) using recomputed blood flow characteristics (e.g., as described in methods 200, 300, 400, or 500, of FIG. 2, 3, 4, or 5, respectively), FIG. 8 may include an exemplary method of performing step 220 of method 200 in FIG. 2. Method 800 may apply the embodiments described in methods 200, 300, 400, and 500 to make more accurate predictions of baseline conditions that could then be used in treatment planning, for example, as described in U.S. Pat. Nos. 8,157,742, 8,594,950, and 8,734,357, which are hereby incorporated by reference herein in their entireties.

Step 802 may include receiving a first set of blood flow characteristics using the simulated contrast distribution. Step 802 may be performed using methods 200, 300, or 400, for determining blood flow characteristics using measured and simulated contrast distribution.

Step 804 may include determining an appropriate plan of treatment based on a received first set of blood flow characteristics. In one embodiment, the appropriate plan of treatment may be determined from the received first set of blood flow characteristics using method 700 as described in FIG. 7. For example, an appropriate plan of treatment may be a percutaneous coronary intervention at the site of a plaque or stenotic lesion. In another example, an appropriate plan of treatment may include administering medications.

Step 806A may include modifying the patient-specific anatomic model to reflect the plan of treatment determined in step 804. Step 806B may include determining a contrast distribution to reflect the plan of treatment.

Step 808 may include computing a second set of blood flow characteristics using the new contrast distribution. Like step 802, step 804 may be performed using methods 200, 300, or 400, for determining blood flow characteristics using measured and simulated contrast distribution.

Step 810 may include reassessing the severity of a plaque or stenotic lesion, based on, one or more of, the patient-specific anatomical model, blood flow characteristics, or hemodynamic forces on the plaque or stenotic lesion. The hemodynamic forces acting on the plaque or stenotic lesion may include, but are not limited to, a stress, a pressure, a force, or a strain on the plaque or stenotic lesion. In one embodiment, step 810 may be performed using method 600 as described in FIG. 6. One or more steps of method 800 may be performed using a processor of server systems 106.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for non-invasively estimating blood flow characteristics, the method comprising:
   receiving information reflecting a measured distribution of a contrast agent delivered through at least a portion of a patient's vasculature;
   constructing a patient-specific anatomic model;
   projecting the measured distribution to the patient-specific anatomic model by averaging a plurality of contrast values of the measured distribution of the contrast agent at a plurality of respective points in a cross sectional area of a vessel to create a patient-specific measured model, the plurality of respective points in the cross sectional area of the vessel including at least a first point in the cross sectional area of the vessel and at least a second different point in the cross sectional area of the vessel;
   defining one or more boundary conditions of a blood flow through one or more points of the patient-specific anatomic model of the patient's vasculature;
   noninvasively generating, using a processor, a patient-specific simulated model of a distribution of the contrast agent through the one or more points of the patient-specific anatomic model using the defined one or more boundary conditions;
   comparing, using a processor, the patient-specific measured model of the measured distribution of the contrast agent and the patient-specific simulated model to determine whether a similarity condition is satisfied;
   updating the defined boundary conditions and re-generating the patient-specific simulated model of the distribution of the contrast agent through the one or more points of the patient-specific anatomic model in an iterative manner, where the updated boundary conditions are used as the boundary conditions for each iterative re-generation, until the similarity condition is satisfied; and
   calculating, using a processor, one or more blood flow characteristics of blood flow through the patient-specific anatomic model using the updated boundary conditions.

2. The computer-implemented method of claim 1, wherein, prior to generating the patient-specific simulated model of the distribution of the contrast agent in the patient-specific anatomic model for a first time, defining the one or more boundary conditions includes relating the patient's vasculature represented by the anatomic model to physiological characteristics found in populations of patients with a similar vascular anatomy.

3. The computer-implemented method of claim 1, wherein, prior to generating the patient-specific simulated model of the distribution of the contrast agent in the patient-specific anatomic model for a first time, defining one or more boundary conditions includes, one or more of:
   assigning an initial contrast distribution; or
   assigning boundary conditions related to a flux of the contrast agent (i) at one or more of vessel walls, outlet boundaries, or inlet boundaries, or (ii) near plaque and/or stenotic lesions.

4. The computer-implemented method of claim 1, wherein the blood flow characteristics include one or more of a blood flow velocity, a blood pressure, a heart rate, a fractional flow reserve (FFR) value, a coronary flow reserve (CFR) value, a shear stress, or an axial plaque stress.

5. The computer-implemented method of claim 1, wherein receiving the information includes receiving one or more images from coronary angiography, biplane angiography, 3D rotational angiography, computed tomography (CT) imaging, magnetic resonance (MR) imaging, ultrasound imaging, or a combination thereof.

6. The computer-implemented method of claim 5, further comprising:
   if the measured distribution of the contrast agent and the patient-specific simulated model of the distribution of the contrast agent satisfy the similarity condition, enhancing the received images using the patient-specific simulated model of the distribution of the contrast agent to create enhanced images; and
   outputting the enhanced images as one or more medical images to an electronic storage medium or display.

7. The computer-implemented method of claim 1, wherein the patient-specific anatomic model is a reduced-order model in a two-dimensional anatomical domain.

8. The computer-implemented method of claim 1, wherein the patient-specific anatomic model includes information related to the patient's vasculature, including one or more of:
   a geometrical description of a vessel, including a length or diameter;
   a branching pattern of a vessel;
   one or more locations of any stenotic lesions, plaque, occlusions, or diseased segments; or
   one or more characteristics of diseases on or within vessels, including material properties of stenotic lesions, plaque, occlusions, or diseased segments.

9. The computer-implemented method of claim 1, wherein the defined boundary conditions pertain to physiological relationships between variables at boundaries of a region of interest, the boundaries including one or more of, inflow boundaries, outflow boundaries, vessel wall boundaries, or boundaries of plaque and/or stenotic lesions.

10. The computer-implemented method of claim 1, wherein generating, using a processor, the patient-specific simulated model of the distribution of the contrast agent for the one or more points in the patient-specific anatomic model using the defined one or more boundary conditions includes one or more of:
    determining scalar advection-diffusion equations governing transport of the contrast agent in the patient-specific anatomic model, the scalar advection-diffusion equations governing the transport of the contrast agent reflecting any changes in a ratio of flow to lumen area at or near a stenotic lesion or plaque; or
    computing a concentration of the contrast agent for the one or more points of the patient-specific anatomic model, wherein computing the concentration requires assignment of an initial contrast distribution and initial boundary conditions.

11. The computer-implemented method of claim 1, wherein satisfying a similarity condition comprises:
    specifying a tolerance that can assess a difference between the measured distribution of the contrast agent and the simulated model of the distribution of the contrast agent prior to generating the patient-specific simulated model of the distribution of the contrast agent; and
    determining whether the difference between the measured distribution of the contrast agent and the simulated model of the distribution of the contrast agent falls within the specified tolerance, the similarity condition being satisfied if the difference falls within the specified tolerance.

12. The computer-implemented method of claim 1, wherein updating the boundary conditions and re-generating the patient-specific simulated model of the distribution of the contrast agent includes mapping a concentration of the contrast agent along vessels with one or more of:
   features derived from an analytic approximation of an advection-diffusion equation describing transport of fluid in one or more vessels of the patient-specific anatomic model;
   features describing an area of a plaque or stenotic lesion; or
   features describing a patient-specific dispersivity of the contrast agent.

13. The computer-implemented method of claim 1, wherein updating the boundary conditions and re-generating the patient-specific simulated model of the distribution of the contrast agent includes using one or more of a derivative-free optimization based on nonlinear ensemble filtering, or a gradient-based optimization that uses finite difference or adjoint approximation.

14. The computer-implemented method of claim 6, wherein enhancing the received images comprises one or more of:
   replacing pixel values with the simulated distribution of the contrast agent; or
   using the patient-specific simulated model of the distribution of the contrast agent to de-noise the received images via a conditional random field.

15. The computer-implemented method of claim 1, further comprising:
   if the measured distribution of the contrast agent and the patient-specific simulated model of the distribution of the contrast agent satisfies the similarity condition, using the calculated blood flow characteristics associated with the patient-specific simulated model of the distribution of the contrast agent to simulate perfusion of blood in one or more areas of the patient-specific anatomic model;
   generating a model or medical image representing the perfusion of blood in one or more areas of the patient-specific anatomic model; and
   outputting the model or medical image representing the perfusion of blood in one or more areas of the patient-specific anatomic model to an electronic storage medium or display.

16. The computer-implemented method of claim 1, wherein the patient-specific anatomic model is represented in a three-dimensional anatomical domain, and wherein creating the patient-specific measured model of the measured distribution of the contrast agent includes assigning contrast values for each point of a three-dimensional finite element mesh.

17. A system for predicting blood flow characteristics, the system comprising:
   a data storage device storing instructions for predicting blood flow characteristics; and
   a processor configured to execute the instructions to perform a method including:
      receiving information reflecting a measured distribution of a contrast agent delivered through at least a portion of a patient's vasculature;
      constructing a patient-specific anatomic model;
      projecting the measured distribution to the patient-specific anatomic model by averaging a plurality of contrast values of the measured distribution of the contrast agent at a plurality of respective points in a cross sectional area of a vessel to create a patient-specific measured model, the plurality of respective points in the cross sectional area of the vessel including at least a first point in the cross sectional area of the vessel and at least a second different point in the cross sectional area of the vessel;
      defining one or more boundary conditions of a blood flow through one or more points of the patient-specific anatomic model of the patient's vasculature;
      noninvasively generating, using a processor, a patient-specific simulated model of the distribution of the contrast agent through the one or more points of the patient-specific anatomic model using the defined one or more boundary conditions;
      comparing, using a processor, the patient-specific measured model of the measured distribution of the contrast agent and the patient-specific simulated model to determine whether a similarity condition is satisfied;
      updating the defined boundary conditions and re-generating the patient-specific simulated model of the distribution of the contrast agent through the one or more points of the patient-specific anatomic model in an iterative manner, where the updated boundary conditions are used as the boundary conditions for each iterative re-generation, until the similarity condition is satisfied; and
      calculating, using a processor, one or more blood flow characteristics of blood flow through the patient-specific anatomic model using the updated boundary conditions.

18. The system of claim 17, wherein, prior to generating the patient-specific simulated model of the distribution of the contrast agent in the patient-specific anatomic model for a first time, defining the one or more boundary conditions includes relating the vasculature represented by the anatomic model to physiological characteristics found in populations of patients with a similar vascular anatomy.

19. The system of claim 17, wherein, prior to generating the patient-specific simulated model of the distribution of the contrast agent in the patient-specific anatomic model for a first time, defining one or more boundary conditions includes, one or more of:
   assigning an initial contrast distribution; or
   assigning boundary conditions related to a flux of the contrast agent (i) at one or more of vessel walls, outlet boundaries, or inlet boundaries, or (ii) near plaque and/or stenotic lesions.

20. A non-transitory computer readable medium for performing a method for use on a computer system containing computer-executable programming instructions for predicting blood flow characteristics, the method comprising:
   receiving information reflecting a measured distribution of a contrast agent delivered through at least a portion of a patient's vasculature;
   constructing a patient-specific anatomic model;
   projecting the measured distribution to the patient-specific anatomic model by averaging a plurality of contrast values of the measured distribution of the contrast agent at a plurality of respective points in a cross sectional area of a vessel to create a patient-specific measured model, the plurality of respective points in the cross sectional area of the vessel including at least a first point in the cross sectional area of the vessel and at least a second different point in the cross sectional area of the vessel;

defining one or more boundary conditions of a blood flow through one or more points of the patient-specific anatomic model of the patient's vasculature;

noninvasively generating, using a processor, a patient-specific simulated model of the distribution of the contrast agent through the one or more points of the patient-specific anatomic model using the defined one or more boundary conditions;

comparing, using a processor, the patient-specific measured model of the measured distribution of the contrast agent and the patient-specific simulated model to determine whether a similarity condition is satisfied;

updating the defined boundary conditions and re-generating the patient-specific simulated model of the distribution of the contrast agent through the one or more points of the patient-specific anatomic model in an iterative manner, where the updated boundary conditions are used as the boundary conditions for each iterative re-generation, until the similarity condition is satisfied; and calculating, using a processor, one or more blood flow characteristics of blood flow through the patient-specific anatomic model using the updated boundary conditions.

* * * * *